United States Patent
Nemoto et al.

(10) Patent No.: US 7,614,879 B2
(45) Date of Patent: Nov. 10, 2009

(54) DENTAL SELF-ETCHING PRIMER

(75) Inventors: Kimiya Nemoto, Tokyo (JP); Norihiro Nishiyama, Tokyo (JP)

(73) Assignee: Nihon University, School Juridical Person, Tokyo (JP)

(*) Notice: Subject to any disclaimer, the term of this patent is extended or adjusted under 35 U.S.C. 154(b) by 126 days.

(21) Appl. No.: 10/482,220

(22) PCT Filed: Jul. 8, 2002

(86) PCT No.: PCT/JP02/06899

§ 371 (c)(1),
(2), (4) Date: Dec. 30, 2003

(87) PCT Pub. No.: WO03/005973

PCT Pub. Date: Jan. 23, 2003

(65) Prior Publication Data

US 2004/0156795 A1 Aug. 12, 2004

(30) Foreign Application Priority Data

Jul. 9, 2001 (JP) ............................ 2001-208015
Feb. 28, 2002 (JP) ............................ 2002-053698

(51) Int. Cl.
A61C 5/00 (2006.01)
A61C 5/04 (2006.01)
A61K 6/00 (2006.01)
A61K 6/08 (2006.01)
A61K 8/00 (2006.01)

(52) U.S. Cl. .................... 433/226; 433/217.1; 523/116; 523/118; 106/35; 424/49

(58) Field of Classification Search .................. 424/49; 523/118
See application file for complete search history.

(56) References Cited

U.S. PATENT DOCUMENTS

| 4,650,847 | A | | 3/1987 | Omura et al. |
| 4,774,349 | A | | 9/1988 | Langerbeins et al. |
| 4,869,828 | A | * | 9/1989 | Hoots et al. .................. 210/701 |
| 5,264,513 | A | * | 11/1993 | Ikemura et al. .............. 526/318 |
| 5,690,840 | A | | 11/1997 | Antonucci et al. |
| 5,922,786 | A | * | 7/1999 | Mitra et al. .................. 523/118 |
| 6,174,935 | B1 | | 1/2001 | Matsunae et al. |
| 2003/0207960 | A1 | * | 11/2003 | Jia .............................. 523/115 |

FOREIGN PATENT DOCUMENTS

| DE | 198 59 989 A1 | 7/1999 |
| EP | 119713 A | 9/1984 |
| EP | 0 246 849 A1 | 11/1987 |
| JP | 10-133421 A | 5/1998 |
| JP | 2001-11350 A | 1/2001 |
| SU | 290031 A | 12/1970 |
| WO | WO 03/035013 A1 | 5/2003 |
| WO | WO 03/068174 A1 | 8/2003 |

OTHER PUBLICATIONS

Suzuki, K. et al., Jounal of Biomedical Materials Research, 1997, 37(2), 261-266.*
Columbia Encyclopedia, http://www.bartleby.com/65/et/ethanol.html, pp. 1-2, Aug. 2000.*
Supplementary Partial European Search Report, EP Application No. 02 74 1442, Sep. 7, 2004.
Suzuki, K et al, Effects of N-methacryloyl amino acid application on hybrid layer formation at the interface of intertubular dentin, J.Dental Research, 1998, vol. 77, No. 11, pp. 1881 to 1888.
Hayakawa, T et al, Efficacy of self-etching primers containing carboxylic acid monomers on the adhesion between composite resin and dentin, J. Oral Science, 1998, vol. 40, No. 1, pp. 9 to 16.
Hayakawa Tooru et al, Study on The Self-etching Prime Containing Carboxylic Acid Monomer, Setcaku Shigaku (Adhesive Dentistry), 1997, vol. 15, No. 3, pp. 211 to 220.
Hasegawa T et al, Investigation of self-etching dentin primers, Dental Material, 1989, vol. 5, No. 6, pp. 408-410.
Nishiyama Norihiro et al, The effects of ph N-methacryloyl glycine primer on bond strength to acid etched dentin, J. Biomedical Materials Research, 1996, vol. 31, No. 3, pp. 379 to 384.
Nishiyama Norihiro et al, Effects of primers on the formation of resin-impregnated layer, DE, J. Dental Engineering, 1996, No. 119, pp. 10 to 13.
Nishiyama, N et al., Adhesion mechanisms to etched-dentin through primer studied by 13C NMR, Polymer Preprints, 1997, vol. 38, No. 2, pp. 147 to 148.

* cited by examiner

*Primary Examiner*—Frederick Krass
*Assistant Examiner*—Lezah W Roberts
(74) *Attorney, Agent, or Firm*—Birch, Stewart, Kolasch & Birch, LLP

(57) ABSTRACT

Bond strength of a composite resin, an adhesive resin cement or the like to dentin or enamel of tooth is remarkably improved by treating the dentin or the enamel with a self-etching primer agent comprising an aqueous solution of a methacrylic acid derivative such as N-methacryloylglycin, N-methacryloyl-3-aminopropionic acid, N-methacryloyl-4-aminobutyric acid, N-methacryloyl-5-aminovaleric acid, N-methacryloyl-6-aminocaproic acid, N-methacryloyl-2-aminomethylphosphonic acid, N-methacryloyl-3-aminoethyl-phosphonic acid and N-methacryloyl-4-aminopropylphosphonic acid.

6 Claims, No Drawings

DENTAL SELF-ETCHING PRIMER

FIELD OF THE INVENTION

The present invention relates to a self-etching primer agent for dental treatment. In more detail, the present invention relates to a self-etching primer agent for dental treatment to be used for surface treatment of dentin or enamel of tooth to which a composite resin is bonded with a bonding agent, or a metal or an orthodontic bracket or the like is bonded with an adhesive resin cement, a dental kit for bonding a dental materials to dentin or enamel of tooth comprising said self-etching primer agent for dental treatment as a component reagent thereof, and a novel methacrylic acid derivative to be used for said self-etching primer agent for dental treatment. In addition, the present invention relates to a method for surface treatment of dentin or enamel of tooth, and use of an aqueous solution of a methacrylic acid derivative for producing a surface treatment agent for dentin or enamel of tooth.

BACKGROUND OF THE INVENTION

Nowadays, in case of bonding a composite resin as a cavity filling material to dentin of tooth with a bonding agent or bonding a metal such as an inlay and a crown to dentin of tooth with an adhesive resin cement, after treating the surface of the dentin of tooth, usually such a method is employed to adhere a bonding agent or an adhesive resin cement to the dentin of tooth, and bond a composite resin through the bonding agent or bond a metal through the adhesive resin cement to the dentin of tooth. The surface treatment of dentin of tooth includes etching treatment and primer treatment. In etching treatment, a surface of dentin is made rugged due to decalcification by dissolving a smear layer and hydroxylapatite of the dentin, followed by penetrating of a bonding agent or an adhesive resin cement into the rugged surface and hardening thereof to enhance their mechanical holding strength and enable to adhere the dentin to the bonding agent or the adhesive resin cement. Primer treatment modifies the dentin of tooth to a suitable state for adhering the bonding agent or the adhesive resin cement.

Such a method for the surface treatment of dentin includes, for instance, a method of etching treatment of dentin with ethylenediamine tetraacetic acid (EDTA) followed by primer treatment with a mixed aqueous solution of glutaraldehyde and 2-hydroxyethylmethacrylate (HEMA) (Munksgaard, E. C., et al., J. Dent. Res., 63(8), 1087-1089, 1984), a method of etching treatment of dentin by deashing with an aqueous solution of orthophosphoric acid, followed by primer treatment for a collagen layer of the dentin with an aqueous solution of HEMA after air drying (Sugisaki, et al., Jpn. J. Conserv. Dent., 34(1), 228-265, 1991; Meerbeek, B. V., et al., J. Dent. Res. 72(2), 495-501, 1993; Pashley, D. H., et al., Quintessence Int. 24(9), 618-631, 1993), and the like.

In order to simplify the surface treatment of dentin, studies have been prevalent on a self-etching primer agent with which both of etching treatment and primer-treatment are performed at the same time. With regard to a self-etching primer agent, for instance, use of N-acryloylaspartic acid (N-AAsp), a derivative of aspartic acid as one of dicarboxylic acids, is proposed as a self-etching primer agent (Ito, et al., Dental Material and Apparatus, 15(4), 341-347, 1996; Ito et al., Dental Material and Apparatus, 16(2), 155-159, 1997; Ito, et al., Dental Material and Apparatus, 16(1), 38-43, 1997). The N-AAsp is considered to decalcify the dentin as an acidic monomer and at the same time act on both of an inorganic material and an organic material in dentin as a functional monomer.

Lately, studies have been prevalent on a self-etching primer agent applicable to both of dentin and enamel (Watanabe, Dental Material and Apparatus, 11(6), 955-973, 1992; Fukushima, et al., Dental Material and Apparatus, 11(4), 679-684, 1992). These self-etching primer agents comprise an acid or an acidic monomer capable of decalcification and a functional monomer to promote diffusion and penetration of a bonding agent. In addition, a mixed aqueous solution of N-methacryloylalanine and HEMA has been proposed as a self-etching primer agent for dentin and enamel (Takahashi, et al., Dental Material and Apparatus, 9(1), 65-73, 1990). With regard to an action mechanism of the agent, it is considered that N-methacryloylalanine decalcifies hydroxyapatite as an acid to make a collagen fiber being exposed, on which HEMA acts as a primer.

On the other hand, it has been reported that a strong adhesion of a composite resin to dentin can be obtained by treating the dentin etched by an aqueous solution of phosphoric acid with an N-methacryloyl-ω-amino acid such as N-methacryloylglycin, N-methacryloyl-4-aminobutyric acid and N-methacryloyl-6-aminocaproic acid as a primer agent (Nishiyama, et al., Dental Material and Apparatus, 13(1), 73-77, 1994; Nishiyama, et al., Dental Material and Apparatus, 17(2), 120-125, 1998). However, use of such an N-methacryloyl-ω-amino acid as a self-etching primer agent has not been so far known.

DISCLOSURES OF THE INVENTION

Thus, an object of the present invention is to provide a self-etching primer agent for dentin or enamel of tooth using such an N-methacryloyl-ω-amino acid, an N-methacryloyl-aminoalkylphosphonic acid, an N-methacryloylaminoalkylsulfonic acid or the like, a dental kit for bonding a dental material to dentin or enamel of tooth comprising said self-etching primer agent as a component reagent and a novel methacrylic acid derivative to be used for said self-etching primer agent.

After an intensive study to obtain a superior self-etching primer agent for dentin or enamel of tooth, the present inventor has found that aqueous solutions of N-methacryloyl-ω-amino acid such as N-methacryloylglycin and N-methacryloyl-5-aminovaleric acid as well as N-methacryloyl-aminoalkylphosphonic acid, N-methacryloylaminoalkylsulfonic acid and the like are exceedingly superior as a self-etching primer agent for dentin or enamel in decalcifying effect for hydroxyapatite of the dentin and the enamel and also in priming effect for an exposed collagen fiber of the dentin and the enamel by decalcification, as well as in much improved bond strength of a bonding agent or an adhesive resin cement to the dentin and the enamel, and accomplished the present invention.

Namely, an aspect of the present invention is a self-etching primer agent for dental treatment to be used for surface treatment of dentin or enamel of tooth, comprising an aqueous solution of a methacrylic acid derivative represented by the formula I below:

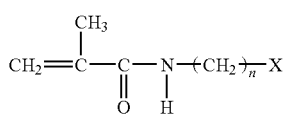

(wherein, n is an integer of 1 to 7; X is —COOH, —PO(OH)$_2$ or —SO$_2$OH).

Further, another aspect of the present invention is a dental kit for bonding a dental material to dentin or enamel of tooth, comprising the above self-etching primer agent for dental treatment as a component reagent thereof.

Still further, another aspect of the present invention is a methacrylic acid derivative represented by the formula I, where X is —PO(OH)$_2$ or —SO$_2$OH.

Still further, another aspect of the present invention is a method for surface treatment of dentin or enamel of tooth, comprising applying a self-etching primer agent for dental treatment comprising an aqueous solution of a methacrylic acid derivative represented by the formula I, to the surface of the dentin or the enamel of tooth.

Still further, another aspect of the present invention is use of an aqueous solution of a methacrylic acid derivative represented by the formula I for producing a surface treatment agent for dentin or enamel of tooth.

BEST MODE FOR CARRYING OUT THE INVENTION

The self-etching primer agent of the present invention is used for surface treatment of dentin or enamel of tooth in case of bonding a composite resin to dentin or enamel with a bonding agent or in case of bonding a metal or an orthodontic bracket to dentin or enamel of tooth with an adhesive resin cement, and has both functions of an etching agent and a primer agent. The self-etching primer agent of the present invention comprises an aqueous solution of a methacrylic acid derivative represented by the above formula I.

Such a methacrylic acid derivative includes N-methacryloyl-ω-amino acids such as N-methacryloylglycin, N-methacryloyl-3-aminopropionic acid (N-methacryloyl-β-alanine), N-methacryloyl-4-aminobutyric acid, N-methacryloyl-5-aminovaleric acid and N-methacryloyl-6-aminocaproic acid; N-methacryloylaminoalkylphosphonic acids such as N-methacryloyl-2-aminomethylphosphonic acid, N-methacryloyl-3-aminoethylphosphonic acid, N-methacryloyl-4-aminopropyl-phosphonic acid, N-methacryloyl-5-aminobutylphosphonic acid and N-methacryloyl-6-aminopentylphosphonic acid; and N-methacryloylaminoalkylsulfonic acids such as N-methacryloyl-3-aminoethylsulfonic acid, N-methacryloyl-4-aminopropylsulfonic acid, N-methacryloyl-5-aminobutylsulfonic acid and N-methacryloyl-6-aminopentylsulfonic acid. Among these, N-methacryloylglycin, N-methacryloyl-3-aminopropionic acid, N-methacryloyl-4-aminobutyric acid, N-methacryloyl-5-aminovaleric acid, N-methacryloyl-6-aminocaproic acid, N-methacryloyl-2-aminomethylphosphonic acid, N-methacryloyl-3-aminoethylphosphonic acid and N-methacryloyl-4-aminopropylphosphonic acid are preferable.

Each of the above N-methacryloyl-ω-amino acids, N-methacryloylaminoalkylphosphonic acids and N-methacryloyl-aminoalkylsulfonic acids may be used alone, or the N-methacryloyl-ω-amino acid may be used in combination with an N-methacryloylaminoalkylphosphonic acid, an N-methacryloylaminoalkylsulfonic acid or a mixture thereof. Said combined use is preferable because the priming effect is particularly improved in addition to the decalcification effect.

Such a methacrylic acid derivative can be synthesized as follows. The N-methacryloyl-ω-amino acid can be obtained by a condensation reaction between a methacrylic halide such as methacrylic chloride and a corresponding ω-amino acid (Nishiyama, et al., Dental Material and Apparatus, 13(1), 73-77, 1994). The N-methacryloylaminoalkylphosphonic acid or the N-methacryloylaminoalkylsulfonic acid can be obtained by a condensation reaction between a methacrylic halide and a corresponding aminoalkylphosphonic acid or a corresponding aminoalkylsulfonic acid, respectively. These N-methacryloyl-aminoalkylphosphonic acid and N-methacryloylaminoalkyl-sulfonic acid are novel compounds.

In the present invention, an aqueous solution of the above methacrylic acid derivative is used as a self-etching primer agent. A suitable concentration of the aqueous solution is usually $10^{-5}$ to 10% by mole, preferably $10^{-3}$ to 8% by mole. The above methacrylic acid derivative is very suitable for a self-etching primer agent because of its high solubility in water. Further, the aqueous solution of a methacrylic acid derivative may be added with ethanol if necessary. In this case, an aqueous solution of ethanol with, for instance, a concentration of 40% or less may be prepared as a self-etching primer agent. The self-etching primer agent of the present invention may be properly added, if necessary, with a polyfunctional monomer or an alcohol, both of which are ordinary additives.

The self-etching primer agent of the present invention may be used for surface treatment of dentin or enamel of tooth usually by applying the aqueous solution thereof to dentin or enamel of tooth after polishing them and reacting for about 10 to 50 seconds, followed by air drying. After the surface treatment, a bonding agent may be applied and then a composite resin may be adhered. A metal or an orthodontic bracket may also be bonded to the dentin or the enamel using an adhesive resin cement. The surface treatment of the dentin or the enamel with the self-etching primer agent of the present invention enables the composite resin, metal and the like to be adhered very firmly.

Each of a bonding agent, a composite resin, an adhesive resin cement, a metal and an orthodontic bracket is not particularly limited, but an ordinary product may be used in a usual manner. An example of the bonding agent includes a bonding agent comprising 10-methacryloyloxy-decamethylenephosphoric acid (MDP) and a polyfunctional monomer; an example of the adhesive resin cement includes a 4-META/MMA-TBB resin obtained by polymerizing methyl-methacrylate (MMA) dissolving 4-methacryloxyethyl-trimellitic anhydride (4-META) with partially oxidized tri-n-butylborane (TBB) in the presence of polymethylmethacrylate (PMMA); and an example of the composite resin includes a composite resin comprising a polyfunctional monomer and silica. With regard to the metal, the metal for dental treatment to be used for an inlay or a crown includes a gold alloy for casting, a gold-silver-palladium alloy for casting and a silver alloy for casting. The orthodontic bracket includes the one usually used.

The self-etching primer agent of the present invention can constitute a dental kit to bond dental materials such as a composite resin, a metal and an orthodontic bracket to tooth, together with a bonding agent, an adhesive resin cement and the like, or together with reagents to prepare them.

The present invention will be described in more detail by Examples hereinbelow, but should not be limited by these Examples.

EXAMPLE 1

Preparation of a Self-Etching Primer Agent

As a self-etching primer agent, 5% by mole of N-methacryloylglycin (NMGly) or N-methacryloyl-5-aminovaleric acid (NMVa) was dissolved in distilled water, to prepare an NMGly solution or an NMVa solution, respectively.

EXAMPLE 2

Measurement of Tensile Bond Strength of a Composite Resin to Dentin and Enamel (1) Method of Adhesion Test Fresh dentin was exposed by smoothly polishing a freshly extracted bovine anterior tooth under sprinkled water with silicon carbide paper (#400 and #600). A polyethylene ring (inside diameter: 3.8 mm, height: 2.0 mm) was temporarily mounted onto the polished surface of dentin, of which an inner surface was treated with the solution of NMGly or NMVa for 30 seconds and dried with air for 10 seconds. Clearfil Megabond (made by KURARAY CO., LTD.) was applied as a bonding agent to the surface, then air-dried (three-way syringe, mild, made by MORITA Corp.) and exposed to light (Quicklight, UL1, made by MORITA Co., Ltd.) for 10 seconds. Immediately after the above procedure, Clearfil AP-X (made by KURARAY CO., LTD.) was filled as a composite resin and exposed to light for 30 seconds to prepare a specimen. The specimen was left for standing at room temperature for 5 minutes and then dipped into water of 37° C.

After dipping for 24 hours, the specimen was taken out of water and subjected to measurement of tensile bond strength of the resin to the dentin. In more detail, after fixing an attachment made of brass to an upper part of the composite resin with a cyanoacrylate adhesive, tensile bond strength was measured under a crosshead speed of 2 mm/min using a universal testing machine (DCS-2000 made by SHIMADZU Corp.) equipped with attachments for bond strength measurement. Ten specimens were prepared for each condition.

In addition, a polished surface of fresh bovine enamel was treated with an NMGly or NMVa solution according to the similar method to the above, to measure bond strength of the composite resin to the enamel.

(2) Results

The bond strengths of the resin to crown dentins and enamels treated with the NMGly or NMVa solution are shown in Table 1.

TABLE 1

Bond strengths of the resin to the crown dentins and the enamels treated with the self-etching primer agents

| | Tensile Bond Strength (MPa) | | | |
| --- | --- | --- | --- | --- |
| | Crown Dentin | SD | Enamel | SD |
| NMGly | 27.9 | 5.1 | 12.3 | 4.5 |
| NMVa | 15.7 | 8.7 | 6.4 | 2.6 |

The bond strengths of the resin to crown dentin was 27.9 MPa for the NMGly solution treatment and 15.7 MPa for the NMVa solution treatment, both showing high values.

On the other hand, the bond strength of the resin to enamel was 12.3 MPa for the NMGly solution treatment, which was higher than the bond strength of 6.4 MPa for the NMVa solution treatment.

From the above results, it was found that the NMGly solution gave a higher bond strength than the NMVa solution.

EXAMPLE 3

Synthesis of N-methacryloylalkylphosphonic acid (1) Synthesis Method

In a reactor equipped with an agitator, 15 ml of water and 0.16 mol of sodium hydroxide were added. Then 0.0045 mol of aminoethylphosphonic acid, aminoethylphosphonic acid or aminopropylphosphonic acid (made by Tokyo Kasei Kogyo Co., Ltd.) was dissolved therein, and the amino group of aminomethylphosphonic acid, aminoethylphosphonic acid or aminopropylphosphonic acid was condensed with methacrylic chloride by dropping 0.045 mol of methacrylic chloride to the above solution while the reactor was cooled with ice. After completion of the reaction, hydrogen chloride gas was introduced while the reactor was cooled by adding methanol (made by Wako Pure Chemical Industries Ltd.) to adjust pH of the reaction layer at 0.4 or less. After separating deposited sodium chloride by filtration, the solution was dried by adding anhydrous sodium sulfate. After filtration, the solvent was distilled off under a reduced pressure. The residue was added with ethyl acetate and ethanol to crystallize N-methacryloyl-2-aminomethylphosphonic acid (NMMP), N-methacryloyl-3-aminoethylphosphonic acid (NMEP) or N-methacryloyl-4-aminopropylphosphonic acid (NMPP) followed by isolation and purification.

(2) Results

The NMR data of the compounds obtained are shown in Table 2 to Table 4.

TABLE 2

Chemical shifts of the $^{13}C$ NMR peaks assigned to NMMP

| $CH_2=$ | >C< | —$CH_3$ | —CO—NH— | $\alpha$-$CH_2$— |
| --- | --- | --- | --- | --- |
| 121.65 | 139.10 | 17.92 | 171.80 | 38.19 |
| | | | | 35.98 |

TABLE 3

Chemical shifts of the $^{13}C$ NMR peaks assigned to NMEP

| $CH_2=$ | >C< | —$CH_3$ | —CO—NH— | $\beta$-$CH_2$— | $\alpha$-$CH_2$— |
| --- | --- | --- | --- | --- | --- |
| 121.266 | 139.45 | 18.56 | 170.27 | 34.61 | 28.36 |
| | | | | | 26.36 |

TABLE 4

Chemical shifts of the $^{13}C$ NMR peaks assigned to NMPP

| CH$_2$= | >C< | —CH$_3$ | —CO—NH— | γ-CH$_2$— | β-CH$_2$— | α-CH$_2$— |
|---|---|---|---|---|---|---|
| 121.25 | 139.29 | 121.24 | 172.07 | 40.31<br>40.04 | 22.41 | 23.14<br>22.41 |

EXAMPLE 4

Synthesis of N-methacryloyl-3-aminoethylsulfonic acid (1) Synthesis Method

In a reactor equipped with an agitator, 15 ml of water and 0.16 mol of sodium hydroxide were added. Then 0.0045 mol of aminoethylsulfonic acid (made by Tokyo Kasei Kogyou Co., Ltd.) was dissolved therein, and the amino group of aminoethylsulfonic acid was condensed with methacrylic chloride by dropping 0.0045 mol of methacrylic chloride to the above solution while the reactor was cooled with ice. After completion of the reaction, hydrogen chloride gas was introduced while the reactor was cooled by adding methanol (made by Wako Pure Chemical Industries Ltd.) to adjust pH of the reaction layer at 0.4 or less. The solvent was distilled off under a reduced pressure. The residue was added with ethyl acetate and ethanol to crystallize N-methacryloyl-3-aminoethylsulfonic acid, followed by isolation and purification.

(2) Results

The NMR data of the compound obtained are shown in Table 5.

TABLE 5

Chemical shifts of the $^{13}$C NMR peaks assigned to N-methacryloyl-3-aminoethylsulfonic acid

| CH$_2$= | >C< | —CH$_3$ | —CO—NH— | β-CH$_2$— | α-CH$_2$— |
|---|---|---|---|---|---|
| 121.72 | 139.10 | 18.40 | 170.26 | 50.33 | 36.35 |

EXAMPLE 5

Measurement of Tensile Bond Strength of the Composite Resin to Dentin and Enamel (1) An aqueous solution of 5% by mole of N-methacryloyl-3-aminopropionic acid (N-methacryloyl-β-alanine) (NMβAla) was prepared similarly as in Example 1. In order to examine performances of the above aqueous solution of NMβAla as well as the aqueous solutions of NMGly and NMVa prepared again in Example 1 as self-etching primer agents, bond strengths of the resin to the crown dentins and the enamels treated with these aqueous solutions were measured similarly as in Example 2. The results obtained are shown in Table 6.

TABLE 6

Bond strengths of the resin to the crown dentins and the enamels treated with the aqueous solutions of NMGly, NMβAla and NMVa

| | Tensile Bond Strength (MPa) | | | |
|---|---|---|---|---|
| | Crown Dentin | SD | Enamel | SG |
| NMGly | 23.6 | 5.1 | 16.0 | 3.3 |
| NMβAla | 24.0 | 3.9 | 2.9 | 1.7 |
| NMVa | 21.2 | 4.8 | 15.0 | 3.6 |

TABLE 6-continued

Bond strengths of the resin to the crown dentins and the enamels treated with the aqueous solutions of NMGly, NMβAla and NMVa

| | Tensile Bond Strength (MPa) | | | |
|---|---|---|---|---|
| | Crown Dentin | SD | Enamel | SG |

As apparent from the results in Table 6, the aqueous solutions of NMβAla, NMGly and NMVa serving as self-etching primer agents improved the bond strength of the resin to crown dentin and enamel.

(2) Each of 0, 0.35, 0.7 and 1.4 mmol of N-methacryloyl-3-aminoethylphosphonic acid (NMEP) synthesized in Example 3 was added to the 5% by mole aqueous solution of NMGly prepared in Example 1, to prepare self-etching primer agents of aqueous solutions of NMGly-NMEP. Bond strengths of the resin to the dentins and the enamels treated with these aqueous solutions were measured. The results obtained are shown in Table 7.

TABLE 7

Bond strengths of the resin to the crown dentin and the enamel treated with the aqueous solutions of NMGly-NMEP

| Amount of NMEP Added | Tensile Bond Strength (MPa) | | | |
|---|---|---|---|---|
| | Crown Dentin | SD | Enamel | SD |
| 0 mmol | 23.6 | 5.1 | 16.0 | 3.3 |
| 0.35 mmol | 24.7 | 5.2 | 15.8 | 4.2 |
| 0.7 mmol | 22.2 | 5.2 | 21.9 | 4.9 |
| 1.4 mmol | 14.1 | 4.9 | 23.8 | 5.5 |

As apparent from the results in Table 7, the addition of NMEP to the 5% by mole aqueous solution of NMGly particularly improved bond strength of the resin to enamel. Judging from the bond strength of the resin to dentin and enamel, an optimum amount of NMEP to be added is estimated to be about 7 mmol.

(3) Similarly, each of 0, 0.35, 0.7 and 1.4 mmol of N-methacryloylethylsulfonic acid (NMES) synthesized in Example 4 was added to the 5% by mole aqueous solution of NMGly, to prepare self-etching primer agents of aqueous solutions of NMGly-NMES. Bond strengths of the resin to the dentins and the enamels treated with these aqueous solutions were measured. The results obtained are shown in Table 8.

TABLE 8

Bond strengths of the resin to the crown dentins and the enamels treated with the aqueous solutions of NMGly-NMES

| Amount of NMES Added | Tensile Bond Strength (MPa) | | | |
|---|---|---|---|---|
| | Crown Dentin | SD | Enamel | SD |
| 0 mmol | 23.6 | 5.1 | 16.0 | 3.3 |
| 0.35 mmol | 12.5 | 5.3 | 14.9 | 2.2 |
| 0.7 mmol | 14.3 | 5.2 | 14.1 | 4.9 |
| 1.4 mmol | 9.5 | 3.5 | 11.9 | 5.0 |

As apparent from the results in Table 8, the addition of NMES to the aqueous solutions of NMGly lowered bond strength of the resin to dentin and enamel.

(4) Self-etching primer agents were prepared by adding 0.7 mmol each of N-methacryloyl-2-aminomethylphosphonic acid (NMMP), N-methacryloyl-3-aminoethylphosphonic acid (NMEP) and N-methacryloyl-4-aminopropylphosphonic acid (NMPP) synthesized in Example 3 to the 5% by mole aqueous solution of NMGly. Bond strengths of the resin to the dentins and the enamels treated with these aqueous solutions were measured. The results obtained are shown in Table 9.

TABLE 9

Bond strengths of the resin to the crown dentins and the enamels treated with the aqueous solutions of NMGly added with each of NMMP, NMEP and NMPP

| | Tensile Bond Strength (MPa) | | | |
|---|---|---|---|---|
| | Crown Dentin | SD | Enamel | SD |
| NMMP | 21.9 | 5.1 | 18.0 | 5.7 |
| NMEP | 22.2 | 5.2 | 21.9 | 4.9 |
| NMPP | 21.0 | 6.2 | 24.4 | 5.2 |

As apparent from the results in Table 9, the bond strength of the resin to enamel was improved more as a chain length of methylene group became longer. The bond strength to dentin remained almost constant.

INDUSTRIAL APPLICABILITY

As described above in detail, bond strength of a composite resin, an adhesive resin cement or the like to dentin or enamel of tooth is remarkably improved when the dentin or the enamel is treated with the self-etching primer agent of the present invention comprising an aqueous solution of a methacrylic acid derivative such as N-methacryloylglycin, N-methacryloyl-3-aminopropionic acid, N-methacryloyl-4-aminobutyric acid, N-methacryloyl-5-aminovaleric acid, N-methacryloyl-6-aminocaproic acid, N-methacryloyl-2-aminomethylphosphonic acid, N-methacryloyl-3-aminoethyl-phosphonic acid and N-methacryloyl-4-aminopropylphosphonic acid prior to bonding of the composite resin, the adhesive resin cement or the like. Consequently, the self-etching primer agent of the present invention is exceedingly superior. Particularly, the self-etching primer agent of the present invention is exceedingly superior as an agent for the treatment of dental diseases such as a root caries, a cervical caries and a direct pulp capping where the bond strength of a composite resin or an adhesive resin cement is crucial.

The invention claimed is:

1. A method for etching and priming dentin or enamel of tooth, consisting of a step of:
    applying a self-etching primer agent for dental treatment consisting of an aqueous solution of (1) at least one ingredient selected from the group consisting of N-methacryloyl-2-aminomethylphosphonic acid, N-methacryloyl-3-aminoethylphosphonic acid, N-methacryloyl-4-aminopropylphosphonic acid and mixtures thereof; and (2) N-methacryloylglycin, and (3) optionally ethanol in an amount up to 40% by weight and (4) optionally a polyfunctional monomer or alcohol,
    to the surface of an unetched dentin or an unetched enamel of a tooth so as to perform both of etching and primer treatments of the unetched dentin or the unetched enamel.

2. The method according to claim 1, wherein a concentration of (1) and (2) in the aqueous solution is $10^{-5}$ to 10% by mole.

3. The method according to claim 2, wherein said concentration is $10^{-3}$ to 8% by mole.

4. The method according to claim 1 or 2, wherein said aqueous solution does not contain said (3) optional ethanol.

5. The method according to claim 1 or 2, wherein said aqueous solution does not contain said (4) optional polyfunctional monomer or alcohol.

6. The method according to claim 4, wherein said aqueous solution does not contain said (4) polyfunctional monomer or alcohol.

* * * * *